United States Patent [19]

Slinkard et al.

[11] 4,192,951

[45] Mar. 11, 1980

[54] HYDROCARBON OXIDATION PROCESS

[75] Inventors: William E. Slinkard; Anthony B. Baylis, both of Corpus Christi, Tex.

[73] Assignee: Celanese Corporation, New York, N.Y.

[21] Appl. No.: 820,663

[22] Filed: Aug. 1, 1977

Related U.S. Application Data

[63] Continuation of Ser. No. 603,979, Aug. 11, 1975, abandoned.

[51] Int. Cl.$^2$ .................. C07C 51/20; C07C 57/14
[52] U.S. Cl. .................. 562/549; 252/432; 252/435; 252/437; 252/439; 252/458; 252/462; 252/465; 252/467; 252/468; 252/469; 252/470; 260/346.75; 562/545; 562/546; 562/547; 562/548

[58] Field of Search .................. 260/533 N; 562/549

[56] References Cited

U.S. PATENT DOCUMENTS 2,625,519  1/1953  Hartig .................. 260/533 N

OTHER PUBLICATIONS

Tsigdinos, Molybdenum Chemicals, Bulletin Cdb-12a (Revised), Nov. 1969, pp. 1-23.

*Primary Examiner*—Vivian Garner
*Attorney, Agent, or Firm*—Linn I. Grim

[57] ABSTRACT

The present invention provides a vapor phase process for high yield conversion of $C_4$-hydrocarbons to maleic acid and acetic acid with a heteropolymolybdic acid catalyst.

13 Claims, No Drawings

HYDROCARBON OXIDATION PROCESS

This is a continuation, of application Ser. No. 603,979, filed Aug. 11, 1975, now abandoned.

BACKGROUND OF THE INVENTION

Processes for the oxidation of organic compounds such as hydrocarbons in the presence or absence of catalysts are well known. There is continuing applied research activity devoted to achieving economically feasible oxidation processes for commercial scale operation.

U.S. Pat. No. 3,282,994 describes a method for the oxidation of butane in liquid phase. U.S. Pat. No. 3,607,925 provides a process for the production of acetic acid by oxidation of butene-2 with nitric acid in the presence of a vanadium catalyst. U.S. Pat. No. 3,644,512 discloses a process for converting butane to acetic acid in liquid phase in the presence of a soluble cobalt compound.

Processes for the oxidation of hydrocarbons in the vapor phase by means of oxygen-containing gases have not proven entirely satisfactory primarily due to the excessive formation of undesirable carbon oxides, and to the difficulty in maintaining control of the highly exothermic oxidation reaction. U.S. Pat. No. 3,395,159 provides an improved process wherein the oxidation of hydrocarbons is performed in a reactor system having fused vanadium oxide catalyst coated on the inner surface of the reactor, which system has the advantage of better temperature control and isothermal operation.

In *J. Am. Chem. Soc.*, 62, 2312(1940) there are reported several processes for vapor phase oxidation of naphthalene to a mixture of partial oxidation products which include naphthoaquinone, phthalic anhydride, maleic anhydride and benzoic acid. The naphthalene oxidation processes are suitable for the production of phthalic anhydride, but are impractical for high yield conversion to maleic anhydride.

In practice the commercial processes for the oxidation of hydrocarbons are difficult to manage, and frequently the yield of desired product is low in comparison to the yield of carbon oxides and other oxidation by-products. The economics of maleic anhydride production by oxidation of butene or benzene is deficient in this respect.

Accordingly, it is an object of the present invention to provide a commercially feasible process for oxidation of hydrocarbons.

It is another object of this invention to provide a vapor phase process for converting $C_4$-hydrocarbons into maleic acid anhydride.

It is another object of this invention to provide a process for oxidizing butane or butene to maleic acid and acetic acid with high conversion efficiency and with a low yield of organic by-products.

It is another object of this invention to provide a process which can be controlled to convert butane into an oxidation product mixture which selectively is predominantly maleic acid or is predominantly acetic acid.

It is a further object of the present invention to provide a novel catalyst composition for vapor phase conversion of $C_4$-hydrocarbons into maleic acid and acetic acid.

Other objects and advantages shall become apparent from the following description and examples.

DESCRIPTION OF THE INVENTION

One or more objects of the present invention are accomplished by the provision of a process which comprises contacting $C_4$-hydrocarbons and oxygen in vapor phase with a heteropolymolybdic acid catalyst.

By the term "heteropolymolybdic acid" is meant a class of heteropoly electrolytes which contain two to eighteen hexavalent molybdenum atoms around one or more central heteroatoms. In some cases, tungsten, vanadium tantalum or niobium replace some of the molybdenum atoms in the structure. In Bulletin Cdb-12a (November, 1969) published by Climax Molybdenum Co. the structure and properties of heteropolymolybdates are described.

Approximately 36 different elements have been reported to function as central heteroatoms. These are exemplified by boron, aluminum, gallium, silicon, germanium, tin, phosphorus, arsenic, antimony, bismuth, selenium, tellurium, iodine, all the first row transition elements from titanium to zinc, second and third row transition elements such as niobium, platinum, cerium, thorium, and other f-group elements as more fully described by D. L. kepert in "Isopolyanions and Heteropolyanions", *Comprehensive Inorganic Chemistry* (Pergamon Press, New York, 1973).

Illustrative of heteropolymolybdates are the phosphopolymolybdates which can be prepared with P:Mo ratios of 1:2, 1:2.5, 1:8.5, 1:9, 1:10, 1:11, 1:12, 2:17 and 2:18.

The heteropolymolybdate anions which have been structurally characterized can be conveniently divided into five broad groups, depending upon the heteroatom:parent atom stoichiometry, and upon the coordination number of the heteroatom.

Group I. 1:12 and 1:11 heteropolymolybdate anions, containing a tetrahedrally coordinated heteroatom. A typical example is $[SiMo_{12}O_{40}]^{4-}$.

Group II. 2:18 and 2:17 heteropolymolybdate anions, which contain tetrahedrally coordinated heteroatoms and are structurally related to the first group. A typical example of a 2:18 anion is $[As_2Mo_{18}O_{62}]^{6-}$.

Group III. 1:6 heteropolymolybdate anions which contain an octahedrally coordinated heteroatom, such as $[TeMo_6O_{24}]^{4-}$.

Group IV. 1:9 heteropolymolybdate anions which contain an octahedrally coordinated heteroatom, such as $[MnMo_9O_{32}]^{6-}$.

Group V. 1:12 heteropolymolybdate anions which contain an icosahedrally coordinated heteroatom, such a $[CeMo_{12}O_{42}]^{8-}$.

The 1:12 heteropolymolybdic acids are the most easily formed and have been the most widely studied. The best known examples are $H_3[PMo_{12}O_{40}]$ and $H_4[SiMo_{12}O_{40}]$. Heteropolymolybdic acids containing up to about 1 atom of tungsten, vanadium, tantalum or niobium per atom of molybdenum can be used in the present process.

Heteropolymolybdic acids have extraordinary solubility in water, and are often soluble in oxygenated organic solvents such as ethers, alcohols and ketones. The crystalline free acids and salts of heteropolymolybdates are usually hydrated. A given acid or salt will often form several solid hydrates. When heated, the heteropolymolybdic acids start losing water of crystallization at about 60° C., followed by complete decomposition at about 400° C.

Throughout specific ranges of pH and other conditions, most solutions of heteropolymolybdic acids appear to contain predominately a distinct species of anion. It is presumed that this predominant species is identical with the anion existing in the solid state.

Heteropolymolybdates are always prepared in solution, generally after acidifying and heating the reactants.

When the central atom is not a transition element, a soluble molybdate may be dissolved with a soluble salt containing the heteroatom in the appropriate oxidation state. The mixture is then acidified to an appropriate pH range. Barium molybdate can be mixed with a sulfuric acid solution containing the heteroatom, or molybdenum trioxide can be boiled with a solution containing the heteroatom.

When the heteroatom is a transition metal, a simple salt of that element can be mixed with a soluble molybdate in a solution of appropriate pH. Alternatively, freshly precipitated hydrous metal oxides can be heated in acidic molybdate solution, or coordination complexes can be decomposed in hot molybdate solution.

The free heteropolymolybdic acids useful as catalysts in the present invention process can be prepared in several ways:

1. By mixing appropriate quantities of the simple acids.
2. By double decomposition of salts, e.g., sulfuric acid plus a barium salt.
3. By extraction with ether from acidified aqueous solutions.
4. By ion exchange of heteropolymolybdate salts.

The preferred catalysts of the present invention are heteropolymolybdic acids which are supported on a suitable inert carrier such as alumina, silica, titanium oxide, diatomaceous earth, carborundum, silica-alumina, boria, or other conventional supports which are inert and do not lower the catalytic activity of the heteropolymolybdic acids.

The preferred catalyst can be prepared by the simple expediency of contacting the carrier substrate with a solution of heteropolymolybdic acid. The content of the heteropolymolybdic acid, based on the weight of molybdenum calculated as the free metal, ranges between about 1.0 and 40 weight percent, based on the total weight of the supported catalyst.

The invention process for oxidizing normal butane and butenes to maleic acid (anhydride) and acetic acid can be conducted in a conventional manner by contacting at high temperatures a $C_4$-hydrocarbon feed stream containing oxygen gas with a heteropolymolybdic acid catalyst in a fixed bed or fluid bed.

The optimum temperature for the reaction system varies between about 180° C. and 350° C., and preferably is in the range between about 225° C. and 300° C. It is an important feature of the present invention process that the process temperature be maintained below about 400° C. so as not to decompose the heteropolymolybdic acid catalyst. It has been found that calcining temperatures above 400° C. convert the molybdenum and other metal components of the heteropolymolybdic acid into the corresponding oxides. As illustrated in Table I hereinbelow, a calcined catalyst has lower catalytic activity, lower efficiency to maleic acid, and promotes an increased yield of by-products such as formic acid.

A suitable contact time between the $C_4$-hydrocarbon feed stream and the heteropolymolybdic acid catalyst can vary between about 0.1 and 10 seconds.

It is desirable that the quantity of oxygen gas in the feed stream be controlled within certain limits to accomplish efficient conversion of the $C_4$-hydrocarbon feed stream to maleic acid and acetic acid. More particularly, the quantity of oxygen gas in the feed stream usually is maintained in the range between about 0.03 and 20 moles per mole of $C_4$-hydrocarbon, and preferably in the hydrocarbon-rich range between about 0.05 and 0.3 mole. Alternatively, the hydrocarbon-lean range between about 4 and 20 moles of oxygen per mole of $C_4$-hydrocarbon can also be employed. Water may be included in the feed stream in a quantity between about 0.05 and 1.0 mole probably about 0.5 to 1.0, per mole of $C_4$-hydrocarbon. Higher proportions of water are not deleterious. The presence of water vapor in the oxidation reaction system increases the efficiency of $C_4$-hydocarbon conversion to maleic acid and acetic acid, although operation in the absence of water is feasible.

The recovery of the product stream and the separation of maleic acid and acetic acid from acetaldehyde, formic acid and other by-products can be accomplished by conventional procedures. U.S. Pat. No. 3,624,148 describes a method for the separation of maleic acid from acetic acid.

The following examples are further illustrative of the present invention. The reactants and other specific ingredients are presented as being typical, and various modification can be devised in view of the foregoing disclosure within the scope of the invention.

VAPOR PHASE OXIDATION PROCEDURES

Standard screening conditions were a feed gas composition ratio of butane/oxygen/steam of 9/1/5 to 11/1/6 with a total flow rate of about 150 ml/min. A pressure of 5–10 psig was maintained in each reactor. The reactor consisted of U-shaped stainless steel tube (inside diameter about 1 cm) with the catalyst-containing section about 55 centimeters long. For supported catalysts, 30 cc of 20/30 mesh material was used. Material balances were calculated over periods of 5–16 hours, and entailed chemical analysis(gas chromatography and titration of acid with base) of liquid products collected in an ice-cooled trap. Oxygen and carbon oxides in the vent were analyzed on a fisher-Hamilton gas partitioner, and samples of the vent gas were analyzed for acetaldehyde and butenes. Examples of catalyst preparations are shown below and results of their use as oxidation catalysts are shown in Table I.

PREPARATION OF CATALYSTS

1. $H_6[P_2Mo_{18}O_{62}]$ On $SiO_2$

| | | |
|---|---|---|
| $MoO_3$ | 144 grams | 1.0 mole |
| $H_3PO_4$ | 8.2 grams | 0.083 mole |
| | | (9.6 grams of 85% $H_3PO_4$) |

$MoO_3$ and $H_3PO_4$ were refluxed together in 1 liter of water overnight and filtered. The unreacted $MoO_3$ residue on the filter was dried and weighed (32.7 grams). The Mo:P ratio of the resulting yellow phosphomolybdic acid was about 9:1. The bright yellow filtrate was concentrated to 200 ml in volume and the remaining water removed by drying in an oven at 80° C. One hundred grams of the dried solid were dissolved in water to form 95 ml of solution. This solution was used to impregnate under vacuum 100 ml/43 grams of macroporous silica beads. The wet beads were dried overnight to yield 94 ml/112 grams of supported catalyst.

$Mo_9PO_x$ On $SiO_2$ For Comparison With Heteropolymolybdic Acid Catalyst

About 30 ml (36 grams) of $H_6[P_2Mo_{18}O_{62}]$ on silica (Catalyst Preparation Reference 1.) was calcined in air (stagnant air muffle furance) at 500° C. for about 16 hours. The resulting solid was placed in a 2 inch outside diameter Vycor tube in a tube furnace, purged with hydrogen, and heated to 400° C. over a period of about 5 hours with a hydrogen flow rate of about 60 ml/min. The temperature was maintained at 400° C. for 16 hours, then the tube and its contents were cooled to room temperature still under a positive flow of hydrogen.

3. $H_4[PMo_{11}VO_{40}]$ On $SiO_2$

| $Na_2MoO_4 \cdot 2H_2O$ | 666 grams | 2.75 moles |
| $NaVO_3 \cdot xH_2O$ | 32.3 grams | 0.25 mole |
| $Na_2HPO_4 \cdot 7H_2O$ | 67.0 grams | 0.25 mole | x=about 0.4

$Na_2HPO_4$ was dissolved in 200 ml of water and added to $NaVO_3$ dissolved in 300 ml of boiling $H_2O$. The solution was cooled, acidified with 25 ml of conc. $H_2SO_4$, and added to $Na_2MoO_4$ dissolved in 400 ml of water followed by 300 ml of conc. $H_2SO_4$. The solution was contacted with ether in a large separatory funnel and the middle layer consisting of the dark red heteropolymolybdic acid-etherate complex was drawn off. The ether was removed on a rotary evaporator to yield a red solid. The solid was dissolved in hot water and part of the solution employed to impregnate 200 ml/84.4 grams of macroporous silica beads. After drying, the final volume and weight of the supported catalyst were 210 ml and 236 grams, respectively.

In a similar manner, in place of vanadium there can be substituted tungsten, tantalum or niobium.

4. $H_4[SiMo_{12}O_{40}]$ On $SiO_2$

| $Na_2MoO_4 \cdot 2H_2O$ | 290.4 grams | 1.2 mole |
| $Na_2SiO_3 \cdot 9H_2O$ | 28.4 grams | 0.10 mole |

$Na_2MoO_4$ was dissolved in 1000 ml of $H_2O$, heated to added $Na_2SiO_3$ dissolved in 250 ml of water at the same time 330 ml of conc. HCl was added. The solution was cooled, contacted with ether in a large separatory funnel, and the bottom layer consisting of the heteropolymolybdic acid-etherate complex drawn off. The ether was removed on a rotary evaporator and the resulting solid was dissolved in a minimum of hot water and employed to impregnate 200 ml/86.7 grams of macroporous silica beads. After drying, the final volume and weight of supported catalyst were 198 ml and 177.3 grams, respectively.

5. $H_5[PMo_{10}V_2O_{40}]$ On $SiO_2$

| $Na_2MoO_4 \cdot 2H_2O$ | 605 grams | 2.5 moles |
| $NaVO_3 \cdot xH_2O$ | 128.2 grams | 1.0 mole |
| $Na_2HPO_4 \cdot 7H_2O$ | 67.0 grams | 0.25 mole | x=about 0.4

$Na_2HPO_4$ was dissolved in 100 ml of water and added to $NaVO_3$ dissolved in 500 ml of boiling water. The solution was cooled and 25 ml of conc. $H_2SO_4$ was added to yield a deep red solution. To this solution was added $Na_2MoO_4$ dissolved in 1000 ml of $H_2O$ followed by 400 ml of conc. $H_2SO_4$. After stirring overnight, the solution was contacted with ether in a large separatory funnel and the middle layer consisting of the heterpolymolybdic acid-etherate complex was separated out. The ether was removed on a rotary evaporator to yield a red solid. The solid was dissolved in hot water and part of the solution was employed to impregnate 250 ml/109 grams of macroporous silica beads. Final volume and weight of the supported catalyst were 244 ml and 281 grams, respectively.

Table I

| | Production Of Maleic Acid And Acetic Acid | | | | |
| Preparation Reference | 1. | | 2. | 3. | 4. |
| --- | --- | --- | --- | --- | --- |
| Catalyst Composition | $H_6[P_2Mo_{18}O_{62}]$ | $Mo_9PO_x/SiO_2$ | | $H_4[PMo_{11}VO_{40}]$ | $H_4[SiMo_{12}O_{40}]$ |
| Reactor Temp., °C. | 274 | 267 | 264 | 266 | 251 |
| Oxygen Conv., % | 99 | 99 | 55–60 | 98–100 | 100 |
| Butane Conv., % | 1.2–1.3 | 2.0–2.7 | 1.5–1.7 | 1.8–2.1 | 1.9 |
| Carbon efficiency*, % | | | | | |
| Butenes | 1.0–1.6 | <1.0 | 3.5–3.7 | <1.0 | <1.0 |
| Acetic Acid | 19–23 | 14–17 | 33 | 25–28 | 28–30 |
| Acetaldehyde | 0.4 | 0.2–0.3 | 1.0–2.3 | 0.6–0.7 | 0.3–0.4 |
| Maleic Acid | 32–35 | 26–29 | 19–21 | 24–26 | 12–13 |
| Acrylic Acid | 0.9–1.3 | 0.5–0.8 | 1.1–1.4 | 3.1–3.6 | 0.6 |
| Formic Acid | 0.1–0.2 | 0.1 | 1.3–1.5 | 0.1–0.2 | <0.1 |
| Carbon Monoxide | 15–16 | 20–23 | 14–15 | 18–21 | 21 |
| Carbon Dioxide | 26–27 | 32–35 | 23–24 | 25–26 | 36 |

*Samples were also analyzed for acetone, formaldehyde, methyl ethyl ketone, 1- and 2-butanols, and propionic and butyric acids. The concentration of these components was low (generally <1%) with no one product predominating.

What is claimed is:

1. The process for producing maleic acid and acetic acid which comprises contacting n-butane and molecular oxygen in the vapor phase at about 180° C. to about 350° C., optionally in the presence of from about 0.05 to about 1.0 mol of water per mol of said n-butane with a heteropolymolybdic acid catalyst consisting essentially of the acids of a class of heteropolyelectrolytes containing 2 to 18 hexavalent molybdenum atoms wherein at least one of said molybdenum atoms can be replaced by an atom selected from the group consisting of tungsten, vanadium, tantalum and niobium, said molybdenum atoms and replacements, if available, being around at least one central heteroatom selected from the group consisting of boron, aluminum, gallium, silicon, germanium, tin, phosphorus, arsenic, antimony, bismuth, selenium, tellurium, iodine, niobium, platinum, cerium, thorium and the first row transition elements from titanium to zinc.

2. A process in accordance with claim 1 wherein maleic acid and acetic acid are produced by contacting n-butane, oxygen and water in the vapor phase with said heteropolymolybdic acid catalyst which is supported on a carrier.

3. A process in accordance with claim 1 wherein the heteropolymolybdic acid catalyst corresponds substantially to the formula:

$$H_6[P_2Mo_{18}O_{62}].$$

4. A process in accordance with claim 1 wherein the heteropolymolybdic acid catalyst corresponds substantially to the formula:

$$H_4[PMo_{11}VO_{40}].$$

5. A process in accordance with claim 1 wherein the heteropolymolybdic acid catalyst corresponds substantially to the formula:

$$H_4[SiMo_{12}O_{40}].$$

6. A process in accordance with claim 1 wherein the heteropolymolybdic acid catalyst corresponds substantially to the formula:

$$H_5[PMo_{10}V_2O_{40}].$$

7. A process for producing maleic acid and acetic acid which comprises contacting butane, from 0.03 to about 20 mols of oxygen per mol of butane and from about 0.05 to about 1.0 mol of water per mol of butane in the vapor phase at a temperature between about 225° C. and 300° C. with a heteropolymolybdic acid catalyst consisting essentially of the acids of a class of heteropolyelectrolytes containing 2 to 18 hexavalent molybdenum atoms wherein at least one of said molybdenum atoms can be replaced by an atom selected from the group consisting of tungsten, vanadium, tantalum and niobium, said molybdenum atoms and replacements, if available, being around at least one central heteroatom selected from the group consisting of boron, aluminum, gallium, silicon, germanium, tin, phosphorus, arsenic, antimony, bismuth, selenium, tellurium, iodine, niobium, platinum, cerium, thorium and the first row transition elements from titanium to zinc.

8. A process in accordance with claim 7 wherein the oxygen is present in a quantity between about 4 and 20 moles per mole of butane.

9. A process in accordance with claim 7 wherein the water vapor is present in a quantity between about 0.5 and 1.0 mole per mole of butane.

10. A process in accordance with claim 7 wherein the heteropolymolybdic acid catalyst contains up to about one atom of tungsten, vanadium, tantalum or niobium, per atom of molybdenum contained therein.

11. A process in accordance with claim 7 wherein the catalyst is phosphopolymolybdic acid corresponding substantially to a formula selected from the group of (a) $H_6[P_2Mo_{18}O_{62}]$ (b) $H_4[PMo_{11}VO_{40}]$ and (c) $H_5[PMo_{10}V_2O_{40}].$ 12. A process in accordance with claim 7 wherein the catalyst is silicopolymolybdic acid corresponding substantially to the formula:

$$H_4[SiMo_{12}O_{40}].$$

13. A process in accordance with claim 7 wherein the contact time of butane with the heteropolymolybdic acid catalyst is between about 0.1 and 10 seconds.

* * * * *